United States Patent
Visser et al.

(10) Patent No.: US 6,551,827 B1
(45) Date of Patent: Apr. 22, 2003

(54) METHODS FOR PRODUCING AND TRANSFORMING CASSAVE PROTOPLASTS

(75) Inventors: Richard Gerardus Franciscus Visser, Bennekom (NL); Christiaan Josef Johannes Raemakers, Arnhem (NL); Evert Jacobson, Wageningen (NL); Johanna Elisabeth Maria Bergervoet van Deelen, Renkum (NL)

(73) Assignee: Cooperatieve Verkoop- en Productievereniging, Ja Veendam (NL)

( * ) Notice: Subject to any disclaimer, the term of this patent is extended or adjusted under 35 U.S.C. 154(b) by 0 days.

(21) Appl. No.: 09/180,481
(22) PCT Filed: May 20, 1997
(86) PCT No.: PCT/NL97/00285
§ 371 (c)(1), (2), (4) Date: Feb. 1, 1999
(87) PCT Pub. No.: WO97/44473
PCT Pub. Date: Nov. 27, 1997

(30) Foreign Application Priority Data

May 20, 1996 (EP) .............................. 96201424

(51) Int. Cl.[7] .............................. C12N 5/00; C12N 5/02
(52) U.S. Cl. .................. 435/421; 435/430; 435/430.1; 435/420; 435/410
(58) Field of Search .................. 800/284; 435/421, 435/430.1, 430, 420, 410

(56) References Cited

U.S. PATENT DOCUMENTS 4,634,674 A * 1/1987 Shahin ...................... 435/240

FOREIGN PATENT DOCUMENTS

| WO | WO 92 11382 A | 7/1992 |
| WO | WO 94 11520 A | 5/1994 |

OTHER PUBLICATIONS

Shahin et al. "Cassava Mesophyll Protoplasts: Isolation, proliferation, and shoot formation". Plant Science Letters, 17(1980) 459–465.*

Cazaux, E. et al. Microcallus formation from *Hevea brasiliensis* protoplasts isolated from embryogenic callus Plant Cell Reports 13 (5): p272–276, 1994.*

Taylor et al. Production of Friable Embryogenic Calli and Suspension Culture Systems in Two Genotypes of Cassava In Second International Scientific Meeting of Cassava Biotechnology Network Bogor Indonesia p 229–240, Aug. 1994.*

Szabados L, et al. Invitro Somatic Embryogenesis and Plant Regeneration of Cassava Plant Cell Reports V6 N3 p. 248–251, 1987.*

Sudarmonowati, E. Somatic embryogenesis and plant regeneration in cassava (*Manihot esculenta* Crantz) Dissertation Abstracts International, vol. 52, No. 7 p. 3378–B, Jan. 1992.*

(List continued on next page.)

*Primary Examiner*—Bruce R. Campell
*Assistant Examiner*—Anne Marie Grunberg
(74) *Attorney, Agent, or Firm*—Hoffmann & Baron, LLP

(57) ABSTRACT

The invention relates to a method for producing protoplasts of cassava or closely related species, which protoplasts are capable of regeneration into plants. The method comprises producing friable embryogenic callus from explants of cassava or closely related species and isolating protoplasts from said friable embryogenic callus. The invention also concerns protoplasts obtainable by said method. The invention further relates to a method for transforming such a protoplast of cassava or closely related species, and transformed protoplasts obtainable thereby. In addition, the invention concerns a method for regenerating plants from these protoplasts and a cassava plant or closely related species obtainable thereby.

9 Claims, 1 Drawing Sheet-

OTHER PUBLICATIONS

Sudarmonowati E. et al. The induction of somatic embryogenesis of recalcitrant cassava cultivars using picloram and dicamba IN: Roca, W.M. and A.M. Thro, eds. Proceddings First International Scientific Meeting of the Cassava Biotechnology Network pp 129–1, Aug. 1992.*

Stamp, JA et al. Somatic Embryogenesis from Clonal Leaf Tissues of Cassava Annals of Botany V59 N4 p445–450, Apr. 1987.*

Biggs, B. et al The use of embryo culture for the recovery of plants from cassava (*Manihot esculenta* Crantz) seeds Plant Cell, Tissue and Organ Culture V6 N3: 229–234, 1986.*

Sudarmonowati, E., et al., "Somatic Embryogenesis and Plant Regeneration in Cassava (*Manihot esculenta* Crantz)", *Dissertation Abstracts International. B, Sciences ABD Engineering*, 52(7):3378B–3379B (1992) (Abstract only).

Raemakers, C.J.J.M., et al., "Cyclic Somatic Embryogenesis and Plant Regeneration in Cassava", *Annals of Botany*, 71(4):289–294 (1993).

Schoepke, C., et al., "Stable Transformation of Cassava Plants (*Manihot esculenta* Crantz) by Particle Bombardment of Embryogenic Suspension Cultures", In Vitro; 32 (3), (PT.2): 67A (1996) (Abstract only).

Konan, N.K., et al., "Optimization of Plant Regeneration from Embryogenic Suspension Cultures of Cassava (*Manihot esculenta* Crantz)", In Vitro, 32 (3) (PT.2): 89–90A (1996) (Abstract only).

Shahin, E.A., et al., "Cassava Mesophyll Protoplasts: Isolation Proliferation and Shoot Formation", *Plant Sci. Lett*, 17(4):459–466 (1980).

Anthony, P., et al., "An Improved Protocol for the Culture of Cassava Leaf Protoplast", *Plant Cell Tissue Organ Culture*, 42:299–302 (1995).

Villegas, L., et al., "Electroporation of Cassava Protoplasts: Pulse Characteristics", In Vitro, 25 (3) (PT.2): 65A (1989) (Abstract only).

Schoepke, C., et al., "Transformation of Cassava (*Manihot esculenta* Crantz) Somatic Embryos Using Particle Bombardment", In Vitro, 29A (3) (PT.2):64A (1993) (Abstract only).

Luong, H.T., et al., "Transient Gene–Expression in Cassava Somatic Embryos by Tissue Electroporation", Plant Science, 107:105–115 (1995).

Raemakers, C.J.J.M., et al., "Production of Transgenic Cassava (*Manihot esculenta* Crantz) Plants by Particle Bombardment Using Luciferase Activity as a Selection Marker", *Molecular Breeding*, 2:339–349 (1996).

Sarria, R., et al., "Agrobacterium Mediated Transformation of Cassava", *Abstracts of Second International Scientific Meeting of the Cassava Biotechnology Network–CBNII*, p. 47 (1995).

Li, H–Q, et al., "Genetic Transformation of Cassava (*Manihot esculenta* Crantz)", *Nature Biotechnology*, 14:736–740 (1996).

Salehuzzaman, S.N.I.M., et al., "Isolation and Characterization of a cDNA Encoding Granule–Bound Starch Synthase in Cassava (*Manihot esculenta* Crantz) and its Antisense Expression in Potato", *Plant Molecular Biology*, 23:947–962 (1993).

Salmoral, E.M., et al., "Comparative Studies of the $\alpha$ 1,4–$\alpha$ 1,6 Glucopolysaccharides from Crops of Commercial Interest", *Chemical Abstracts*, 121(3):842 (1994) (Abstract only).

* cited by examiner

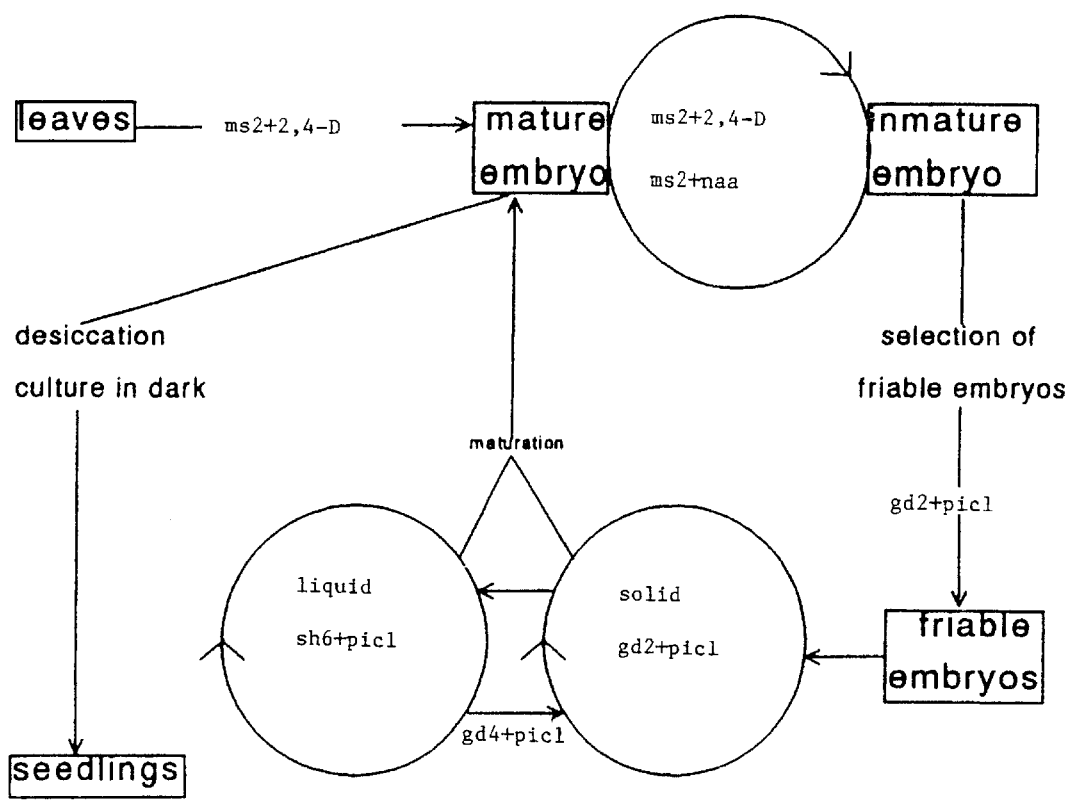

METHODS FOR PRODUCING AND TRANSFORMING CASSAVE PROTOPLASTS

This application claims the benefit of International Application Number PCT/NL97/00285 filed on May 20, 1997 which is incorporated herein by reference.

BACKGROUND OF THE INVENTION

Genetic modification or transformation is the technique wherein one or a few gene(s) are added to a commercial interesting genotype or clone. In principle a successful transformation system requires an efficient system where new plants are formed from specific plant parts (stem, leaf, node and so on) or from protoplasts (single cells without cell wall) derived of these parts, a system to transfer DNA molecules to the plant's parts or protoplasts and a system to select tissue and plants which contain and express the introduced gene(s).

In principle protoplasts are the most ideal system for DNA delivery. They can be cultured as single cells that produce multicellular colonies from which plants develop. Plants derived from protoplasts are generally clonal in origin. This provides a useful tool for any transformation system, because it will eliminate chimerism in transgenic plants.

Cassava is very recalcitrant for plant regeneration of protoplasts. There is only one report of shoot regeneration from protoplasts of cassava (Shahin and Shephard, 1980). They used well expanded leaves for the isolation of protoplasts. Despite considerable efforts, plant regeneration from protoplasts (isolated from leaves, stems, and roots) has never been repeated since then (Anonymus, 1985; Nzoghe, 1991; Anthony et al., 1995, Sofiari, 1996). A logical approach was to use tissues which contain embryogenic cells. Such cells are found in the apical meristems, young leaves or somatic embryos cultured on auxin supplemented media (Stamp and Henshaw, 1987a; Raemakers et al., 1993a). However, protoplasts isolated from these tissues gave in the best case green callus and adventitious roots (Sofiari, 1996). Recently, a new type of somatic embryogenesis was developed. In this in vitro system the embryos do not develop beyond the (pre-)globular stage and the embryogenic callus is highly friable (Taylor et al., 1995). Transfer of this friable embryogenic callus (FEC) to liquid medium resulted in a suspension-like culture. In leek (Buitenveld and Creemers, 1994), petunia (Power et al., 1979), rice (Kyozuka et al., 1988), sugarcane (Chen, et al., 1988), and wheat (Chang et al., 1991) such cultures were an excellent source for protoplast regeneration.

We have now found that in cassava FEC is the only tissue from which protoplasts can be isolated which are able to regenerate into plants sofar.

SUMMARY OF THE INVENTION

Thus the present invention provides a method for producing protoplasts of cassava or a closely related species, which protoplasts are capable of regeneration into plants, comprising producing friable embryogenic callus from explants of cassava or a closely related species and isolating protoplasts from said friable embryogenic callus. It appears, as will be described below, that for obtaining suitable protoplasts the culture in solution of the FEC is quite important. Therefore the present invention further provides a method wherein the friable embryogenic callus is subjected to culture in a liquid medium.

Protoplasts are preferably produced by subjecting plant cells to enzymatic breakdown of the cell walls. The invention thus provides a method whereby a mixture of cell wall degrading enzymes, such as a cellulase, a pectolyase and/or a macerozyme are used to produce protoplasts.

It also appears that the method according to the invention works best when the plants from which explants are to be taken are pretreated. Therefore the invention provides a method whereby the plants from which explants are taken are pretreated with an auxin as described below.

On the explants preferably embryogenesis is induced resulting in an invented method whereby the friable embryogenic callus is produced from torpedo shaped primary or mature embryos. The reason is explained in the detailed description. Protoplasts obtainable by a method as disclosed above are also part of the invention.

An important reason for wanting to have protoplasts which can be regenerated into plants is of course that protoplasts can be easily transformed or transduced or provided with additional genetic information by any other suitable method. Thus one is now able to provide cassava plants or closely related species with genetic material of interest. The invention thus also provides a method for transforming (defined as providing with in any suitable manner) a protoplast of a cassava or a closely related species by providing said protoplast with additional genetic information through infection by a bacterium comprising said additional genetic information such as *Agrobacterium tumefaciens*, by electroporation or chemical poration providing a vector comprising said additional genetic information or by particle bombardment whereby the particles are coated with the additional genetic information, whereby a protoplast obtainable from friable embryogenic callus is transformed. The invention also encompasses transformed protoplasts obtainable by such a method.

Below a short introduction is given on the usefulness of transforming plants, such as cassava.

Application of plant gene technology encompasses a multitude of different techniques ranging from isolation of useful genes, their characterization and manipulation, to the reintroduction of modified constructs into the plants (Lonsdale, 1987). Plant gene technology will catalyze progress in plant breeding, as is exemplified by a few examples of transgenic crops like rice (Chen et al., 1987; Shimamoto et al., 1989), maize (Gordon-Kamm et al., 1990; Vain et al., 1993), wheat (Marks et al., 1989), and potato (De Block, 1988; Visser et al., 1989). Rapid progress in gene technology has allowed insight into the complex molecular mechanism of plant pathogen recognition and the natural defence strategies of host plants. This technology can also be used for controlled and efficient identification of desirable genotypes, far beyond the possibilities of classical breeding.

For instance electroporation of protoplasts derived from suspension cultures led to the transformation of maize (Rhodes et al., 1988), rice (Toriyama et al., 1988) and orchardgrass (Horn et al., 1988).

Successful attempts have been made to improve resistance against pathogenic viruses like tobamovirus in tobacco (Powel Abel et al., 1986), potexvirus in potato (Hoekema et al., 1989) and in papaya (Fitch et al., 1992). In the above examples the introduced trait was based on expressing of single genes that are coding for the coat protein. In cassava, African cassava mosaic virus (ACMV) and cassava common mosaic virus (CCMV) may be controlled by the coat protein-mediated resistance technique (Fauquet et al., 1992). The genes encoding key enzymes of cyanogenesis have been cloned (Hughes et al., 1994) which makes manipulation of cassava cyanogenesis by genetic transformation using the antisense approach feasible. Another embodiment of the invention is the manipulation of starch in the cassava tubers.

Thus the present invention provides a transformed protoplast whereby the additional genetic information comprises an antisense construct, particularly one whereby the antisense construct is capable of inhibiting the amylose synthesis pathway.

A protoplast cannot grow in the field, nor can it be harvested. Though protoplasts are necessary for transformation, it must be possible to regenerate said protoplasts into embryos and/or plants. This is a very important embodiment of the invention, because cassava has been shown to be difficult to regenerate from protoplasts. The detailed description explains how this may be achieved. For further information reference is made to the thesis written by E. Sofiari titled Regeneration and Transformation of Cassava (Manihot Esculenta Crantz.), a copy of which is enclosed with the present application, which is as yet unpublished and which is incorporated herein by reference. Thus the invention provides a method for regenerating plants from protoplasts whereby a protoplast according to the invention is induced to produce an embryo, which embryo is consequently induced to produce a plant.

The plants obtainable by said method are also part of the invention, in particular plants whereby the tubers contain essentially no amylose.

BRIEF DESCRIPTION OF THE DRAWING

FIG. 1: Schematic representation of somatic embryogenesis in cassava, including primary, secondary somatic embryogenesis, selection of friable embryogenic callus, maturation and desiccation followed by germination.

gd2=medium supplemented with Gresshoff and Doy salts (1974) and vitamins plus 20 g/l sucrose.

gd4=medium supplemented with Gresshoff and Doy salts (1974) and vitamins plus 40 g/l sucrose.

ms2=medium supplemented with Murashige and Skoog salts and vitamins plus 20 g/l sucrose.

pic=10 mgl/l Picloram, NAA=10 mg/l naphthalene acetic acid, 2,4-D=8 mg/l, 2,4-dichlorophenoxy acetic acid.

sh6=medium supplemented with Schenk and Hildebrandt (1972) salts and vitamins plus 60 g/l sucrose.

Detailed Description
Initiation of FEC

The procedure to obtain FEC is outlined in FIG. 1. It starts with the induction of primary embryos. Primary embryos are formed in a two step procedure. In the first step explants are cultured on medium supplemented with salts and vitamins (preferably Murashige and Skoog (1962)), a carbohydrate source (for example 20 g/l sucrose) and an auxin (e.g. 1–8 mg/l picloram, or dicamba or 2,4-D) for the initiation of embryos. After 10 to 15 days on this first medium bipolar torpedo shaped embryos are formed. Torpedo shaped embryos possess a clear hypocotyl and cotyledon primordia. After transfer of the explants with torpedo shaped embryos to a step 2 medium (the same medium as step 1 but without an auxin) the torpedo shaped embryos become mature. Mature embryos possess large green cotyledons.

Zygotic embryos (Stamp and Henshaw 1982; Konan et al., 1994), young leaf explants or apical meristems (Stamp and Henshaw, 1987a; Szabados et al., 1987; Mroginsky and Scocchi, 1993; Raemakers 1993a; Narayanaswamy et al., 1995) and floral tissue (Mukherjee, 1995) can be used to obtain primary embryos. In this way many different genotypes were evaluated for their ability to form primary embryos. In this protocol primary somatic embryos were only formed after culture on solid medium and never after culture in liquid medium. Furthermore, somatic embryos (primary) were only observed if the auxins Picloram, Dicamba or 2,4-D were used and not with IAA, IBA or NAA.

In the presently used protocol there is genotypic variation in the number of mature embryos formed per cultured explant. The genotypes M.Col1505, M.Col22 and Gading gave the highest numbers of mature embryos per cultured leaf explant (ME/CLE). However, the number of mature embryos formed was low. In M.Col22 a maximum of 22% of the leaf explants isolated from in vitro grown plants and cultured on a step 1 medium with 4 mg/l 2,4-D, formed ME with a maximum number of 0.8 ME/CLE. On a step 1 medium with 8 mg/l 2,4-D a maximum of 49% of the leaf explants formed ME with a maximum number of 3.5 ME/CLE. Higher 2,4-D concentrations did not further improve the embryogenic capacity of explants.

In an attempt to improve the capacity of leaf explants to produce primary somatic embryos, donor plants were grown under different conditions. Growth of in vitro donor plants under different light regimes (8, 12, 16 or 24 hours) had no influence on the embryogenic response. However, a reduction of the light intensity had a positive effect. The best results were obtained with leaf explants isolated of donor plants grown at 8 $\mu Em^{-2}s^{-1}$ and cultured on a step 1 medium.

Other investigators have shown that in certain genotypes, Dicamba (1–66 mg/l) and Picloram (1–12 mg/l) are superior to 2,4D for inducing primary embryogenesis (Ng 1992; Sudarmonowati and Henshaw, 1993; Taylor and Henshaw, 1993). Mathews et al. (1993) improved the efficiency of primary embryogenesis in the genotype M.Col1505 by transferring explants after 15 days of step 1 medium to a growth regulator-free medium supplemented with 0.5% charcoal. On this medium maturation was improved and as a result the number of mature embryos increased from 0.4 in the control to 3.4 ME/CLE.

The best results were obtained if donor plants were pretreated with auxins as 2,4-D or picloram or Dicamba. For this, plants were grown in liquid MS20 medium and supplied with the auxin (final concentration 8 mg/l) after 12 days of growth. Two days later leaf explants were isolated of the donor plants and cultured on step 1 medium with 8 mg/l 2,4-D, picloram or Dicamba. In the clone M.Col22 this resulted in a production of 9.4 ME/CLE. This was significantly higher than in the $H_2O$-treated control-plants, where 3.5 ME/CLE were produced (Table 3).

The general applicability of the auxin pretreatment was tested on several different genotypes. Without a pretreatment of donor plants two genotypes formed ME and at low frequency. After a pretreatment of donor plants, leaf explants of almost all genotypes formed ME.

Eventually we were able to obtain mature primary somatic embryos from 18 of the 22 tested genotypes (Table 1, except TMS30221, TMS30001, TMS30572 and Sao Paolo).

Primary somatic embryos derived from zygotic embryos and from leaves have been used as explants to initiate secondary embryos (Stamp and Henshaw, 1987b; Szabados et al., 1987; Mathews et al., 1993; Raemakers et al., 1993bc; Luong et al., 1995). Continuous culture of somatic embryos on auxin supplemented medium resulted in a cyclic system of somatic embryogenesis. The way of subculturing somatic embryos for secondary embryogenesis seemed to influence the morphology of the embryogenic tissue. Clumps of somatic embryos recultured monthly on solid 2,4D containing medium in the dark developed into finger-like embryo initials formed on the top of older embryos. The embryos did not pass the torpedo-shaped stage.

Further development occurred if the clumps with embryos were transferred to step 2 medium in the light (Szabados 1987). Normally mature somatic embryos were cultured in step 1 medium in the light and twenty days later the explants were transferred to step 2 medium for maturation. In this system embryos developed to maturity and mature embryos with large green cotyledons were used to start a new cycle of embryogenesis whereas in the system of others torpedo shaped embryos were used to start a new cycle of secondary somatic embryogenesis.

This system of multiplication of mature embryos has been tested in 14 of the in Table 1 mentioned genotypes. Despite the fact that in most genotypes only a few mature primary embryos were available, all genotypes, except one, gave new mature embryos after culture on 2,4-D supplemented medium, in a much higher frequency as observed for primary somatic embryogenesis. Embryogenicity was maintained by regular subculture of mature embryos for more than one year (Szabados et al., 1987; Mathews et al., 1993; Raemakers, 1993). New somatic embryos were formed both in liquid and solid medium. In all the genotypes it was observed that in liquid medium more embryos were formed than in solid medium and that fragmentation of embryos before the start of a new cycle of secondary somatic embryogenesis increased the production compared to whole embryos. In for example M.Col22 whole embryos cultured on solid medium produced 8 embryos per cultured embryo, whereas fragmented embryos cultured in liquid medium produced 32 embryos per cultured embryo (Raemakers et al., 1993c). Not only, 2,4-D, Picloram and Dicamba, but also NAA had the capacity to induce secondary embryogenesis. IBA and IAA did not induce secondary embryogenesis. NAA has been used successfully in Adira 1, Adira 4, Gading, Line 11, M.Col22, M.Col1505, TMS90853 and Gading. In general more mature embryos were produced in NAA supplemented medium than in 2,4-D, Picloram or Dicamba supplemented medium. Furthermore, the development of NAA induced embryos was faster than with 2,4-D, Dicamba or Picloram. Shortening the culture duration has a beneficial effect, particularly, when operating on a large scale.

Histologically, the by 2,4-D newly induced secondary embryos were attached vertically to the explants whereas those by NAA were horizontally.

There is still a problem in obtaining embryogenic cultures of cassava (Mroginski and Scocchi, 1992; Taylor et al., 1992; Narayanaswamy et al., 1995; Sudarmonowati and Bachtiar, 1995). The main problem is not that embryogenic tissue from primary explants can be obtained, but the large scale multiplication of this tissue by secondary embryogenesis. For this purpose, either tissue consisting of torpedo shaped embryos or mature embryos can be used. Multiplication of torpedo shaped embryos is highly genotype dependent, while multiplication of mature embryos is largely genotype independent (Raemakers, 1993). Both primary and secondary somatic embryogenesis are characterized by the formation of propagules with a bipolar structure. These bipolar torpedo shaped embryos are already formed on the auxin supplemented step 1 medium. Therefore, Taylor et al., (1995) proposed the term organized embryogenesis. Organized cells are defined as a group of actively dividing cells, having the tissues and organs formed into a characteristic unified whole (Walker, 1989).

A less organized type of somatic embryogenesis was developed by Taylor et al. (1995). With continuous selection, organized embryogenic tissue cultured on a Gresshoff and Doy (1972) medium salts and vitamins supplemented with 10 mg/l Picloram (GD2) converted gradually into a less organized tissue. This tissue consisted of a callus-like mass of (pro-)globular embryos which was very friable. Therefore, this tissue was called friable embryogenic callus (FEC). The cells in FEC are continuously in a state where they break away from group control and because of that they are not organized into a unified structure. FEC is maintained on a medium consisting of Gresshoff and Doy (1972) vitamins and salts, 7 g/l Daichin agar, 20 g/l sucrose and 10 mg/l Picloram (solid GD2). Every three weeks the friable embryos were subcultured on the above mentioned medium. In order to initiate liquid suspension cultures 0.5 g of friable embryos was transferred in a flask of 200 ml with 50 ml of liquid medium supplemented with Schenk and Hildebrandt (1972) salts and vitamins, 60 g/l sucrose and 10 mg/l Picloram (liquid SH6). The medium was refreshed every 2 days and after 14 days the content of each flask was divided over 5 new flasks. The pH was adjusted to 5.7 before autoclaving. The temperature in the growth chamber was 30° C., the photoperiod 12 hours and the irradiance 40 $\mu$molm$^{-2}$s$^{-1}$. Suspension cultures were initiated by culturing FEC in Schenk and Hildebrandt (1972) medium supplemented with 6% (w/v) sucrose and 10 mg/l Picloram (SH6). Every 2–3 days this medium was refreshed.

To keep a culture in a highly friable state the FEC has to be sieved once in two months. In practice the part of the FEC which will go through a sieve with a mesh of 1 mm$^2$ will be used for subculture.

FEC will almost never form torpedo shaped embryos on the GD2 or in SH6 medium. Torpedo shaped and subsequent mature embryos are formed if FEC is cultured on maturation medium. Maturation medium consist of Murashige and Skoog (1962) salts and vitamins, 0.1 g/l myo-inositol, 20 g/l sucrose, 18.2 g/l mannitol, 0.48 g/l MES, 0.1 g/l caseinhydrolysate, 0.08 g/l adenosine sulphate, 0.5 mg/l d-calcium-panthotenate, 0.1 mg/l choline chloride, 0.5 mg/l ascorbic acid, 2 mg nicotinic acid, 1 mg/l pyridoxine-HCl, 10 mg/l thiamine HCl, 0.5 mg/l folic acid, 0.05 mg/l biotin, 0.5 mg/l glycine, 0.1 mg/l L-cysteine, 0.25 mg/l riboflavine and 1 mg/l picloram. This maturation medium was refreshed every 3 weeks.

Mature embryos could be induced into secondary somatic embryogenesis by culturing on MS20 medium supplemented with 2,4-D, picloram, Dicamba or NAA. Primary and secondary somatic embryogenesis are relatively easy to establish in a wide range of genotypes (see Table 1), while FEC is for the time being restricted to a few genotypes. The prospect of FEC for a new system of somatic embryogenesis and genetic transformation is promising, although further research is needed to make this system applicable to more genotypes. Essential for this process is the availability of high quality organized tissue and the ability of this tissue to convert into FEC. Taylor et al. (1995) "used organized embryogenic tissues" which were multiplied at the torpedo shaped state to initiate FEC. In this case two steps (initiation of organized. tissue and conversion into unorganized tissue) are determinative for the successful initiation of FEC. Both steps are genotype dependent. If organized tissue is multiplied in the mature state as described by Raemakers (1993) then only the ability of this tissue to convert into FEC is a determinative step to initiate FEC. It remains to be investigated whether or not organized tissue can be used as starting material. If organized tissue cannot be used, then this tissue should be first multiplied in the immature state before it can be used to initiate FEC. This is readily accomplished by, either culturing explants at a high density or by reducing the cyclic duration.

Regeneration of Plants from Protoplasts
Isolation of Protoplasts

For protoplast isolation both FEC cultured on solid GD2 or liquid SH6 can be used. However, the highest yield of protoplasts was obtained from FEC which has been cultured for 1 to 3 weeks in liquid SH6.

Two gram of FEC was placed in Petri dishes (Ø 9 cm) containing 10 ml of cell wall digestion solution. Cell wall digestion solution consisted of a mixture of cell wall degrading enzymes; 10 mg/l pectolyase, 10 g/l cellulose, 200 mg/l macero enzym growth regulators (NAA 1 mg/l, 2,4-D 1 mg/l, Zeatin 1 mg/l); major salts (368 mg/l $CaCl_2$; 34 mg/l $KH_2PO_4$; 740 mg/l $KNO_3$; 492 mg/l $MgSO_4.7H_2O$); minor salts (19.2 mg/l NA-EDTA; 14 mg/l $FeSO_4.7H_2O$) and osmoticum (91 g/l D-mannitol) and 0.5 g/l MES. The cell wall degrading enzymes cellulase (1–10 g/l) plus Macerozyme (200 mg/l) were successful for protoplast isolation. The extra addition of Pectolyase (0.001–0.01 g/l) and/or Driselase (0.02 g/l) increased the yield of protoplasts. After 18 h of incubation, 10 ml of washing medium was added to the solution. Washing medium with an osmolarity 0.530 mOsm/kg consisted of major salts (see cell wall digestion solution), 45.5 g/l mannitol and 7.3 g/l NaCl. The digested tissue was filtered through a 73 $\mu$M pore size filter (PA 55/34 Nybolt—Switzerland) into a 250 ml beaker glass. The filtrate was divided equally over two 12 ml conical screw cap tubes, and centrifuged at 600 rpm for 3 min. (Mistral 2000). The washing procedure was repeated once after removal of the supernatant. The protoplast solution was resuspended by floating on 9.5 ml solution containing major and minor salts (see cell wall digestion solution) and 105 g/l sucrose. The pH was 5.8 and the osmolarity 0.650 mOsm. The solution with protoplasts was allowed to equilibrate for 5 minutes before 0.5 ml of washing medium was gently added on the top. After centrifugation at 700 rpm for 15 min. (Mistral 2000), the protoplasts were concentrated in a band between the sucrose and washing medium. The protoplast layer was harvested with a pasteur pipette and the yield was counted in a standard haemocytometer chamber.

Protoplast Culture

Protoplasts were cultured in media solidified with agarose 0.2% w/v (Dons en Bouwer, 1986) in petri dishes containing 10 ml of the same liquid medium. The following media resulted in the formation of micro callus:

TM2G medium (Wolters et al., 1991) supplemented with only auxins (0.1–10 mg/l NAA or 0.1–10 mg/l Picloram, or 0.1–10 mg/l IAA, or 0.1–10 mg/l 2,4-D, or 0.1–10 mg/l Dicamba, or 0.1–10 mg/l, or 0.1–10 mg/l) or auxins plus cytokinins (0.01–1 mg/l zeatin, 0.01–1 mg/l 2-iP, 0.01–1 mg/l BA, 0.01–1 mg/l TDZ, 0.01–1 mg/l kinetin).

medium A (Murashige and Skoog (1962) salts and vitamins, 4.5 g/l myo-inositol, 4.55 g/l mannitol, 3.8 g/l xylitol, 4.55 g/l sorbitol, 0.098 g/l MES, 40 mg/l adeninsulphate and 150 mg/l caseinhydrolysate, 0.5 mg/l d-calcium-panthotenate, 0.1 mg/l choline-chloride, 0.5 mg/l ascorbic acid, 2.5 mg/l nicotinic acid, 1 mg/l pyridoxine-HCl, 10 mg/l thiamine-HCl, 0.5 mg/l folic acid, 0.05 mg/l biotine, 0.5 mg/l glycine, 0.1 mg/l L-cysteine and 0.25 mg/l riboflavine and 59.40 g/l glucose) supplemented with only auxins (0.1–10 mg/l NAA or 0.1–10 mg/l Picloram, or 0.1–10 mg/l IAA, or 0.1–10 mg/l 2,4-D, or 0.1–10 mg/l Dicamba plus cytokinins (0.01–1 mg/l zeatin, 0.01–1 mg/l 2-iP, 0.01–1 mg/l BA, 0.01–1 mg/l TDZ, 0.01–1 mg/l kinetin).

The media were refreshed every 10 days, by replacing 9 ml with fresh medium. After two months of culture in the first medium, high quality FEC was selected and either culture for further proliferation or for maturation. For proliferation FEC was transferred to Gresshoff and Doy (1974) medium supplemented with 40 g/l sucrose, 7 g/l Daichin agar and 2 mg/l picloram (GD4). After 3 weeks the FEC was transferred to a Gresshoff and Doy medium supplemented with 20 g/l sucrose, 7 g/l agar and 10 mg/l Picloram (GD2). Suspension cultures ware initiated by transferring 1.0 g of FEC to liquid SH6% medium supplemented with 10 mg/l Picloram. Two weeks later the suspension was divided over new flasks with an initial packed cell volume of 1.0 ml.

After 2 months of culture, $10^4$ protoplasts cultured in TM2G supplemented with 0.5 mg/l NAA and 1 mg/l Zeatin at a density of $10^5$/ml produced 1058 micro-calli, whereas $10^4$ protoplasts cultured at a density of $10^6$/ml only produced 64 micro-calli.

Replacing TM2G medium with medium A reduced at both densities the number of micro-calli significantly. At this stage at least three types of calli could be distinguished. One type consisted of globular shaped embryos which were mostly observed in protoplasts cultured at a density of $10^6$. Some of them developed cotyledon like structures, light green in color. However, these embryos could not be germinated properly. Another type was fast growing and consisted of a large compact callus, they were observed in protoplast cultures of both densities. This callus never developed embryos. The third type was highly friable callus and was observed at both densities. At a density of 2–5×$10^5$ (medium TM2G) about 60% of the calli were friable and embryogenic. The FEC was either subcultured for further proliferation or for maturation.

Proliferation of FEC Derived from Protoplasts

Following selection of FEC, 0.1 g of it cultured for three weeks on GD 4 plus 2 mg/l Picloram increased into 0.7 g of tissue. More than 95% of the tissue consisted of high quality FEC. Subsequently, this tissue was maintained by subcultures of three weeks on GD2 medium supplemented with 10 mg/l Picloram. To initiate suspension cultures FEC was transferred to liquid medium. The increase in packed cell volume (PCV) of this material was slightly higher than that of the original material (data not shown).

Maturation of FEC Derived from Protoplasts

In an attempt to induce maturation of embryos, FEC isolated after two months of culture in TM2G was cultured on maturation medium. Maturation medium consisted of Murashige and Skoog (1962) salts and vitamins, 0.1 g/l myo-inositol, 20 g/l sucrose, 18.2 g/l mannitol, 0.48 g/l MES, 0.1 g/l caseinhydrolysate, 0.08 g/l adenine sulphate, 0.5 mg/l d-calcium-panthotenate, 0.1 mg/l choline chloride, 0.5 mg/l ascorbic acid, 2. mg/l nicotinic acid, 1 mg/l pyridoxine-HCl, 10 mg/l thiamine HCl, 0.5 mg/l folic acid, 0.05 mg/l biotin, 0.5 mg/l glycine, 0.1 mg/l L-cysteine, 0.25 mg/l riboflavine and 1 mg/l picloram. This maturation medium was refreshed every 3 weeks.

On this medium there is a gradual shift from proliferation to maturation. As a result the packed cell volume had increased with a factor 4 after two weeks of culture in liquid maturation medium. Also after transfer to solid maturation medium there is proliferation. After two weeks on solid medium most of the embryos had reached a globular shape and only a few of these globular embryos developed further.

The first torpedo shaped embryos became visible after one month of culture on solid maturation medium. The number of mature and torpedo shaped embryos was not correlated with the plating efficiency but with the density of the initially cultured protoplasts. No such embryos were obtained if protoplasts were cultured on TM2G without growth regulators. The highest number of mature and torpedo shaped embryos was formed from protoplasts cultured on TM2G supplemented with 0.5 mg/l NAA and 1 mg/l Zeatin. If NAA was replaced by Picloram then the number of torpedo shaped and mature embryos was significantly lower (Table 2). From the tested Picloram concentrations 2 mg/l gave the best results. After 3 months of culture between 60 and 200 torpedo shaped and mature embryos were isolated per agarose drop. Torpedo shaped embryos became mature at high frequency if they were cultured on fresh maturation medium or on MS2 plus 0.1 mg/l BAP.

Secondary Somatic Embryogenesis and Germination of Mature Embryos Derived from Protoplasts Only a few torpedo shaped embryos formed secondary embryos if cultured on liquid or solid MS2 medium supplemented with 10 mg/l NAA or 8 mg/l 2,4-D (data not shown). Mature embryos were better explants for secondary embryogenesis. In both liquid and solid medium 2,4-D was superior for induction of secondary embryogenesis as compared to NAA. If mature embryos were first cultured in 2,4-D and then in liquid NAA the response was comparable with culture in 2,4-D alone. Also embryos which first had undergone a cycle of secondary somatic embryogenesis in medium with 2,4-D, produced highly efficient secondary embryos in MS20 supplemented with 10 mg/l NAA.

The germination of cyclic or secondary somatic embryos, induced in liquid medium by the auxins 2,4-dichlorophenoxyacetic acid (2,4-D) or naphthalene acetic acid (NAA), was compared. In all genotypes desiccation stimulated normal germination of NAA induced embryos. However, the desiccated embryos, required a medium supplemented with cytokinins such as benzytaminopurine (BAP) for high frequency germination. The morphology of the resulting seedling was dependent on the concentration of BAP. With 1 mg/l BAP plants with thick and short taproots and branched shoots with short internodes were formed. With 0.1 mg/l BAP the taproots were thin and slender and the shoot had only one or two apical meristems. If the embryos were desiccated sub-optimally, higher concentrations of BAP were needed than if the embryos were optimally desiccated to stimulate germination. Also desiccated embryos which were cultured in the dark required a lower concentration of BAP and, furthermore, these embryos germinated faster than embryos cultured in the light. Complete plants were obtained four weeks after the start of somatic embryo induction. 2,4-D induced embryos showed a different response. In only one genotype desiccation enhanced germination of 2,4-D induced embryos and in three other genotypes it did not. In all genotypes desiccation stimulated root formation. Embryos cultured in the dark formed predominantly adventitious roots, whereas embryos cultured in the light formed predominantly taproots.

Gene Transfer Systems

Over the past years several transfer techniques of DNA to plant protoplasts have been developed such as silicon fibers (Kaeppler et al., 1990), microinjection (De Laat and Blaas, 1987) and electrophoresis (Griesbach and Hammond, 1993). The most commonly used and potentially-applicable ones are Agrobacterium-mediated gene delivery, microprojectile/particle bombardment and protoplast electroporation.

The *Agrobacterium tumefaciens* DNA delivery system is the most commonly used technique. It probably relates to the first invention of DNA delivery in plants by this method. Initially it was limited to Kalanchoe and Solanaceae, particularly tobacco. Nowadays, the use of Agrobacterium-mediated transformation has changed dramatically, it is possible to transform a wide range of plants with a limitation in monocots (reviewed by Wordragen and Dons, 1992).

Although cassava is a host for Agrobacterium it has proven to be not highly amenable to it.

In principle protoplasts are the most ideal explants for DNA delivery. They can be cultured as single cells that produce multicellular colonies from which plants develop. Plants derived from protoplasts are generally clonal in origin. This provides a useful tool for any transformation system, because it will eliminate chimerism in transgenic plants. The use of protoplasts is, however, hampered by the regeneration system which is highly species dependent. For transformation, protoplasts can be used in conjunction with PEG to alter the plasma membrane which causes reversible permeabilization that enables the DNA to enter the cytoplasm as was demonstrated, for example, in *Lolium multiform* (Potrykus et al., 1985) and *Triticum monococcum* (Lörz et al., 1985). Another technique to increase the permeability of plasma membranes and even cell walls to DNA is by electroporation (for review see Jones et al., 1987). In this method electrical pulses enable the DNA to enter the cells. Rice was the first crop in which fertile transgenic plants resulted from protoplast electroporation (Shimamoto et al., 1989).

The use of particle bombardment or biolistics to deliver foreign DNA provides an alternative method in cassava transformation. Particle bombardment is the only procedure capable of delivering DNA into cells almost in any tissue. The first transgenic plant obtained by using this method was in tobacco (Klein et al., 1989). Following this successful transformation method, particle bombardment is widely used in plants which are less amenable to Agrobacterium infection, particularly monocots. Improvement of several DNA delivery devices to accelerate the particle (microprojectile) has resulted in the most recent model the Biolistic™ PDS-1000 (Bio-Rad Laboratories, Richmond, Calif.). Those devices are available commercially, however the price is relatively high at present. Tungsten or gold particles, coated with DNA, are commonly used as microprojectiles to deliver DNA into the target tissue (recently reviewed by Songstad et al., 1995).

Selection and Reporter Genes Used in Genetic Modifications

To be able to identify transformed cells, the gene of interest is coupled to a selectable marker gene. This marker gene is necessary to select transformed cells. Selection can be based on a visual characteristic of the transformed cell/tissue. An example is the luciferase gene isolated from the firefly. Plant cells expressing this gene and supplied with substrate (luciferin) will emit light which can be detected with special equipment (Ow et al., 1986). Another way to select transformed tissue is the introduction of a gene which encodes resistance to antibiotics or herbicides (Thompson et al., 1987; Gordon-Kamm et al., 1990).

A number of antibiotics and herbicides has been used as selective agent in plant transformation. In cereals resistance to the herbicide phosphinothricin (PPT) was chosen for the selection of transgenic plants (Cao et al., 1990). In *Carica papaya* (Fitch et al., 1994), *Vitis vinifera* (Nakano et al., 1994; Scorza et al., 1995), maize (Rhodes et al., 1988) and rice (Chen et al., 1987) the neomycine phosphothansferase (NPTII) gene, which confers resistance to kanamycin and related antibiotics (Fraley et al., 1986), was used as a selectable marker.

In cassava all above-mentioned systems of selection can be used, however PPT based selection has as advantage that it improves the ability of FEC to form mature embryos and in this way increase plant regeneration.

TABLE 1

Genotypes of cassava used for somatic embryogenesis.

| Indonesia | Nigeria | TMS90853 | M. Co122, |
|---|---|---|---|
| Adira 1 | TMS50395 | TMS30555 | Zimbabwe |
| Tjurug | TMS60444 | TMS30211 | Line 11 |
| Adira 4 | TMS90059 | TMS30395 | Venuzuela |
| Mangi 4 | TMS30572 | TMS30001 | M.Ven77 |
| Gading | TMS4(2)1244 | Columbia | Brasil |
| Faroka | TMS60506 | M. Col 1505 | Sao Paolo |

TABLE 2

Influence of light intensity during growth of donor plants in vitro on the number of leaf explants responding with the formation of mature embryos and the number of mature embryos per cultured leaf explant (#ME/CLE).

| light intensity ($\mu Em^{-2}s^{-1}$) | number of explants | responding explants[a] | production (# ME/CLE[b]) |
|---|---|---|---|
| 40 | 48 | 18 b | 1.7 b |
| 28 | 48 | 26 ab | 4.9 ab |
| 8 | 48 | 31 a | 6.6 a |

[a,b]means with the same letter are not significantly different by respectively Chi-square test ($p < 0.1$) and by LSD test ($p < 0.1$)

TABLE 3

Influence of 2,4-D pretreatment on production of primary mature embryos (# mature embryos per cultured leaf explant isolated from in vitro plants), followed by the multiplication of mature embryos by secondary somatic embryogenesis in 11 Nigerian cassava genotypes and in M.Co122.

| embryogenesis | primary[a] | | secondary[b] |
|---|---|---|---|
| 2,4-D pretreatment | no | yes | |
| M.Co122 | 3.5 | 9.4 | 13.5 |
| TMS 30555 | 0 | 0.7 | 6.2 |
| TMS 50395 | 0 | <0.1 | 5.3 |
| TMS 60506 | 0 | <0.1 | 0 |
| TMS 90059 | 0 | <0.1 | 7.2 |
| TMS 30211 | 0 | 0 | — |
| TMS 60444 | 0 | 1.1 | 9.9 |
| TMS 30395 | 0 | 0.1 | 6.7 |
| TMS 90853 | <0.1 | 0.2 | 8.2 |
| TMS 4(2)1244 | <0.1 | 0 | 5.4 |
| TMS 30001 | 0 | 0 | — |
| TMS 30572 | 0 | 0 | — |

[a]average of three experiments (total 48–74 leaf explants),
[b]average of two experiments (total 24–48 ME explants).

Cited Literature

Anonymus, 1985. CIAT: Annual report: Centro International de Agricultura Tropical, Cali, Columbia. Pp: 197–217.

Anthony, P., Davey, M R., Power, J. B,, and Lowe, K. C. 1995. An improved protocol for the culture of cassava leaf protoplasts. Plant Cell Tissue and Organ Culture. 42:229–302

Buiteveld, J., and Creemers-Molenaar, J. 1994. Plant regeneration from protoplasts isolated. from suspension cultures of leek (*Allium ampeloprasum* L.). Plant Science. 100:203–210.

Cao, J., Duan, X., McElroy, D., and Wu, R. 1990. Regeneration of herbicide resistant transgenic rice plants following microprojectile-mediated transformation of suspension culture cells. Plant Cell Rep. 11: 586–591.

Chang, Y. F., Wang, W. C., Colleen, Y. W., Nguyen, H. T., and Wong, J R. 1991. Plant regeneration from protoplasts isolated from long-term cell cultures of wheat (*Trilicum aestivum*). Plant Cell Rep. 9:611–614.

Chen, W. H., Davey, M R., Power, J. B., and Cocking, E. C. 1988. Sugarcane protoplasts: factors affecting division and plant regeneration. Plant Cell Rep. 7:344–347.

Chen, W. H., Gartland, K. M. A., Davey, M R., Sotak, R., Gartland, J. S., Mulligan, B. J., Power, J. B., and Cocking, E. C. 1987. Transformation of sugarcane protoplasts by direct uptake of a selectable chimeric gene. Plant Cell Rep. 6:297–301.

DeLaat, A., and Blaas, J., 1987. An improved method for protoplast microinjection suitable for transfer of entire plant chromosomes. Plant Sci 50:161–169.

Fitch, M. M. M., Pang, S. Z., Slightom, Lius. S., Tennant, P., Manshardt, R. M., and Gonsalves, D. 1994. Genetic transformation in *Carica papaya* (Papaya). In: Bajai (Eds). Biotechnology in Agriculture and Forestry Vol. 29. Plant protoplasts and genetic engineering V. Springer-Verlag, Berlin. P:237–255.

Dons, J. J. M., and Bouwer, R. 1986. Improving the culture of cucumber protoplasts by using an agarose-disc procedure. Proceedings of an international symposium on nuclear techniques and in vitro culture for plant improvement. Jointly organized by the International Atomic Energy Agency and the Food and Agriculture Organization of the United Nations. Held in Vienna, Aug. 19–23, 1985. P:498–504.

Fraley R. T., Rogers S. G., and Horsch, R. B. 1986. Genetic transformation in higher plants. CRC Critical reviews in Plant Sciences 4(1):1–46.

Gordon-Kamm, W. J., Spencer, T M, Mangano, M. R., Adams, T. R., Daines, R. J., William, G. S., OBrien, J. V., Chambers, S. A. Adams, Jr. W. R., Willetts, N. G., Rice, T. B., Mackey C. J., Krueger, R. G., Kausch, A. P. and Lemaux P. G. 1990. Transformation of maize cells and regeneration of fertile transgenic plants. The Plant Cell. 2:603–618.

Gresshoff, P. M., and Doy, C. H. 1974. Development and differentiation of haploid *Lycopersicon esculentum* (tomato). Planta 107:161–170.

Griesbach, R. J., and Hammond, J. 1993. Incorporation of the GUS gene into orchids via embryo electrophoresis. Acta. Hort. 336:165–169.

Horn, M. E., Shillito, R. D., Conger, B. V., and Harms, C. T. 1988. Transgenic plants of, orchardgrass (*Dactylis glomerata* L.) from protoplasts. Plant Cell Rep. 7:469–472.

Hovenkamp-Hermelink, J H M, De Vries J N, Admase P, Jacobsen E, Withold B, Feenstra W J, 1988. Rapid estimation of the amylose/amylopectine ration in small amounts of tuber and leaf tissue of potato. Potato Res. 31: 241–246.

Kaeppler, H. F., Gu, W., Somres, D. A., Rines, H. W., Cockburn, A. F. 1990. Silicon carbide fiber-mediated DNA delivery into plant cells. Plant Cell Rep. 8:415–418.

Klein T. M., Kornstein L., Sanfords J. C., and Fromm M E. 1989. Genetic transformation of maize cells by particle bombardment. Plant Physiol. 91:440–444.

Konan N. K., Sangwan R. S., and Sangwan-Norren. 1994. Nodal axillary meristems as target tissue for shoot production and genetic transformation in cassava (*Manihot esculenta* Crantz). Second International Scientific Meeting of Cassava Biotechnology Network 11. Bogor. Indonesia. p:276–288.

Kyozuka, J., Otoo; E., and Shimamoto, K. 1988. Plant regeneration from protoplasts of indica rice: genotypic differences in culture respond. Theor. Appl. Genet. 76:887–890.

Lörz, H., Baker, B., and Schell, J. 1985. Gene transfer to cereal cells mediated by protoplast transformation. Mol. Gen. Genetic 199: 178–182.

Luong, H. T., Shewry, P. R., and Lazzeri, P. A. 1994. Gene transfer to cassava somatic embryos via tissue electroporation and particle bombardment. In: Second International Scientific Meeting of Cassava Biotechnology Network 11. Bogor. Indonesia. p:303–314.

Mathews, H., Carcamo, R., Chavarriaga, Schopke, C. P., Fauquet, C. and Beachy, R. N., 1993. Improvement of somatic embryogenesis and plant recovery in cassava. Plant Cell Rep. 12:328–333.

Mroginski and Scocchi, 1992. Somatic embryogenesis of Argentine cassava varieties. In: Roca, W. M., and Thro, A. M. (Eds). Proceedings First Scientific Meeting of the Cassava Biotechnolgy Network. Cartagena, Colombia Aug. 25–28, 1992. P:175–179.

Mukherjee, A. 1994. Embryogenesis and regeneration from cassava Galli of anther and leaf. The Cassava Biotechnology Network. Proceeding of the Second International Scientific Meeting. Bogor, Indonesia, Aug. 22–26, 1994 P:375–377, Murashige, T., and Skoog, F. 1962 A revised medium for rapid growth and bioassay with tobacco cultures. Physiol. Plantarum 15 473–497.

Nakano, M., Hoshino, Y., and Mil, M. 1994. Regeneration of transgenic plants of grapevine (*Vitis Vinifera* L.) via Agrobacterium rhizogenesis-mediated transformation of embryogenic calli. J. of Exp. Bot. 45 (274):649–656.

Narayanaswamy, T. C., Ramaswamy, N. M., and Sree Rangaswamy, S R. 1995. Somatic embryogenesis and plant regeneration in cassava. The Cassava Biotechnology Network. Proceeding of the Second International Scientific Meeting. Bogor, Indonesia, Aug. 22–26, 1994. P:324–329.

Ng S Y C (1992) Tissue culture of root and tuber crops at IITA. In: Thottappilly G, Monti L M, Mohan Raj D R, Moore A W (eds), Biotechnology: enhancing research on tropical crops in Africa CTA/IITA co-publication, IITA, Ibadan, Nigeria, pp 135–141.

Nzoghe, D. 1989. Recherche de conditions permettant l'obtention neoformations chez differents genotypes de manioc (*Manihot esculenta* Crantz). Extension a la culture de protoplastes. These. Universite De Paris Sud Centre D'Orsay. P: 119.

Ow, D. W., Wood, K. V., DeLuca, M., De Wet, J R., Helinski, D R., and Howell, S. H. 1986. Transient and stable expression of the firefly luciferase gene in plant cells and transgenic plants. Science 234:856–859.

Potrykus, I, Saul, M., Paskowski, J., and Shillito, R. D. 1985. Direct gene transfer into protoplasts of a graminacious monocot. Mol. Gen.Genet. 199:183–188.

Power, J. B., Bery, S. F., Chapman J. V., and Cocking, E. C. 1979. Somatic hybrids between unilateral cross-incompatible Petunia species. Theor. Appi. Genet. 55: 97–99.

Raemakers, C. J. J. M. 1993. Primary and cyclic somatic embryogenesis in cassava *Manihot esculenta* Crantz. PhD thesis Agricultural University Wageningen, The Netherlands. P:119.

Raemakers, C. J. J. M., Bessembinder, J., Staritsky, G., Jacobsen, E., and Visser, R. G. F. 1993a. Induction, germination and shoot development of somatic embryos in cassava. Plant Cell Tissue and Organ Culture 33:151–156.

Raemakers, C. J. J. M., Amati, M., Staritsky, G., Jacobsen, E., and Visser, R. G. F. 1993b. Cyclic somatic embryogenesis and plant regeneration in cassava. Annals of Bot. 71:289–294.

Raemakers, C. J. J. M., Schavemaker, C. M., Jacobsen, E., and Visser, R. G. F. 1993c. Improvements of cyclic somatic embryogenesis of cassava (*Manihot esculenta* Crantz). Plant Cell Rep. 12:226–229.

Rhodes, C. A., Pierce, D. A., Metier, I. J., Mascarenhas, D., and Detmer, J. J. 1988. Genetically transformed maize plants Erom protoplasts. Science 240:204–207.

Scorza, R., Cordts, J. M., Ramming, D. W., and Emershad, R. L. 1995. Transformation of grape (*Vitis vinifera* L.) zygotic-derived somatic embryos and regeneration of transgenic plants. Plant Cell Rep 14:589–592.

Shahin, E. A., and Shepard, J. F. 1980. Cassava mesophyll protoplasts: isolation, proliferation and shoot formation. Plant Science Letters 17:459–465.

Shenk, R. U. and Hildebrandt, A. C., 1972, Medium and techniques for induction and growth of monocotyledonous and dicotyledonous plant cell cultures. Can. J. Bot 50:99/

Shimamoto, K., Terada, R., Izawa, T., and Fujimoto, H. 1989. Fertile transgenic rite plants regenerated from transformed protoplasts. Nature 338:274–276.

Sofiari, E, 1996. Regenration and transformation in cassava *Manihot esculenta* Crantz. PhD thesis Agricultural University Wageningen, The Netherlands. P:136.

Songstad, D. D., Somers, D. A., and Griesbach, R. J. 1995. Advances in alternative DNA delivery techniques. Plant Cell Tissue and Organ Culture 40:1–15.

Stamp, J. A., and Henshaw, G. G. 1987a. Somatic embryogenesis from clonal leaf tissue of cassava. Annals of Bot. 59:445–450.

Stamp, J. A. 1987. Somatic embryogenesis in cassava: the anatomy and morphology of the regeneration process. Annals of Bot. 59: 451–459. Stamp, J. A., and Henshaw, G. G. 1987b. Secondary somatic embryogenesis and plant regeneration in cassava. Plant Cell Tissue and Organ Culture 10:227–233;

Stamp, J. A., and Henshaw, G. G. 1982. Somatic embryogenesis in cassava. Zeitschrift für Pflanzenphysiologie. 105:183–187.

Sudarmonowati and Bachtiar, 1995. Induction of somatic embryogenesis in Indonesian cassava genotypes. The Cassava Biotechnology Network. Proceeding of the Second International Scientific Meeting. Bogor, Indonesia, Aug. 22–26, 1994. P:364–374).

Sudarmonowati. E., and G. G. Henshaw. 1992. The induction of somatic embryogenesis of recalcitrant cultivars using picloram and dicamba. In: Roca, W. M., and Thro, A. M. (Eds). Proceedings First Scientific Meeting of the Cassava Biotechnology Network. Cartagena, Colombia Aug. 25–28, 1992. P:128–133.

Szabados L., Hoyos R. and Roca W. 1987. In vitro somatic embryogenesis and plant regeneration of cassava. Plant Cell Rep. 6:248–251.

Taylor, N. J., Clarke, M., and Henshaw, G. G. 1992. The induction of somatic embryogenesis in fifteen African cassava cultivars. In: Roca, W. M., and Thro, A. M. (Eds). Proceedings First Scientific Meeting of the Cassava Biotechnology Network. Cartagena, Colombia Aug. 25–28, 1992. P:134–137.

Taylor, N. J., Edwards, M., and Henshaw, G. G. 1995. Production of friable embryogenic calli and suspension culture system in two genotypes of cassava. Second International Scientific Meeting of Cassava Biotechnology Network 11. Bogor. Indonesia. P:229–240.

Thompson, J. C., Movva, N. R., Tizard, R., Crameri, R., Davies, J. E., Lauwereys, M., and Botterman, J. 1987. Characterization of the herbicide-resistance gene bar from

*Streptomyces hygroscopicus*. The EMBO J.6 (9):2319–2523.

Toriyama, K., Arimoto, Y., Uchimiya, H., and Hinata, K. 1988. Transgenic rice plants after direct gene transfer into protoplasts. Bio/Technology. 6:1072–1074.

Visser R G F, Hergersberg M, van der Ley F R, Jacobsen E, Witbolt B, Feenstra W J, 1989. Molecular cloning and partial characterization of the gene for granula-bound starch synthase from a wild type and a amylose-free potato. Plant Sci 64185–192.

Visser R G F, Stolte A, Jacobsen E, 1991. Expression of a chimeric granula-bound starch synthase-GUS gene in transgenic potato tubers. Plant Physiol 82:411–416.

Walker, P. M. B. 1989. Chambers Biology Dictionary. W&R Chamber Ltd. Clay Ltd, St. Ives Plc. England. P:205.

Wolters, A. M. A., Schoenmakers, H. C. H., van der Meulen-Muiser, J. J. M., van der Knaap, E., Derks, F. H. M., Koornneef, M., and Zelcer, A. 1991. Limited DNA elimination from the irradiated potato parent in fusion products of albino *Lycopersicon esculentum* and *Solanum luberosum*. Theor. Appl. Genet. 83:225–232.

Wordragen M. F., and Dons, HINL 1992. *Agrobacterium tumefaciens* mediated transformation of recalcitrant crops. Plant Mol. Biol. Reporter 10:12–36.

What is claimed is:

1. A method for producing protoplasts of cassava comprising producing friable embryogenic callus from explants of cassava and isolating protoplasts from said friable embryogenic callus, wherein the protoplasts are capable of regenerating into complete plants.

2. A method according to claim 1 whereby the friable embryogenic callus is subjected to culture in a liquid medium.

3. A method according to claim 1 whereby a mixture of cell wall degrading enzymes are used to produce protoplasts.

4. A method according to claim 2 whereby a mixture of cell wall degrading enzymes are used to produce protoplasts.

5. A method according to one of claims 1–4 whereby the plants from which the explants are taken are pretreated with an auxin.

6. A method according to one of claims 1–4 whereby the friable embryogenic callus is produced from torpedo shaped primary or mature embryos.

7. A method according to claim 6 whereby the embryos are induced on primary explants.

8. A method according to claim 3 wherein the enzymes are a cellulase, a pectolyase and/or a macerozyme.

9. A method for producing protoplasts of cassava comprising:

(a) inducing embryogenesis on cassava explants to produce embryogenic tissue;

(b) producing friable embryogenic callus from said embryogenic tissue; and (c) isolating protoplasts from said friable embryogenic callus, wherein the protoplasts are capable of regenerating into complete plants.

* * * * *

UNITED STATES PATENT AND TRADEMARK OFFICE
CERTIFICATE OF CORRECTION

PATENT NO. : 6,551,827 B1
DATED : April 22, 2003
INVENTOR(S) : Visser et al.

It is certified that error appears in the above-identified patent and that said Letters Patent is hereby corrected as shown below:

<u>Title page,</u>
Item [73], Assignee:, now reads "Cooperatieve Verkoop- en Productievereniging, Ja Veendam (NL)" should read -- Coöperative Verkoop- en Productievereniging, van Aardappelmeel en Derivaten AVEBE B.A., Ja Veendam (NL) --

Signed and Sealed this

Sixth Day of April, 2004

JON W. DUDAS
*Acting Director of the United States Patent and Trademark Office*